(12) United States Patent
Skluzacek et al.

(10) Patent No.: US 6,514,530 B2
(45) Date of Patent: *Feb. 4, 2003

(54) DOSAGE FORM COMPRISING MEANS FOR CHANGING DRUG DELIVERY SHAPE

(75) Inventors: Robert R. Skluzacek, Newark, CA (US); David E. Edgren, El Granada, CA (US)

(73) Assignee: ALZA Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,402

(22) Filed: Aug. 5, 1998

(65) Prior Publication Data

US 2002/0006439 A1 Jan. 17, 2002

Related U.S. Application Data

(60) Provisional application No. 60/058,323, filed on Sep. 9, 1997.

(51) Int. Cl.[7] .................................................. A61K 9/22
(52) U.S. Cl. ........................ 424/468; 424/470; 424/473
(58) Field of Search .................. 424/464, 465, 424/468, 472, 473, 474, 469, 470

(56) References Cited

U.S. PATENT DOCUMENTS

| | | | |
|---|---|---|---|
| 2,799,241 A | 7/1957 | Wurster | 118/240 |
| 3,133,132 A | 5/1964 | Loeb et al. | 264/49 |
| 3,173,876 A | 3/1965 | Zobrist | 252/137 |
| 3,276,586 A | 10/1966 | Rosaen | 210/90 |
| 3,541,005 A | 11/1970 | Strathmann et al. | 210/19 |
| 3,541,006 A | 11/1970 | Bixler | 210/23 |
| 3,546,876 A | 12/1970 | Fokker et al. | 60/24 |
| 3,845,770 A | 11/1974 | Theeuwes | 128/260 |
| 3,916,899 A | 11/1975 | Theeuwes | 128/260 |
| 4,063,064 A | 12/1977 | Saunders et al. | 219/121 |
| 4,088,864 A | 5/1978 | Theeuwes | 219/121 M |
| 4,111,202 A | 9/1978 | Theeuwes | 128/260 |
| 4,160,020 A | 7/1979 | Ayer et al. | 424/15 |
| 4,200,098 A | 4/1980 | Ayer et al. | 128/260 |
| 4,285,987 A | 8/1981 | Ayer et al. | 427/3 |
| 4,327,725 A | 5/1982 | Cortese et al. | 128/260 |
| 4,612,008 A | 9/1986 | Wong et al. | 604/892 |
| 4,783,337 A | 11/1988 | Wong et al. | 424/468 |
| 4,863,456 A | 9/1989 | Stephens et al. | 604/892.1 |
| 4,902,514 A | 2/1990 | Barclay et al. | 424/473 |

OTHER PUBLICATIONS

Encyclopedia of Polymer Science and Engineering, Supplement vol., Acid–Base Interactions to Vinyl Chloride Polymers pp 568–573, (1989), published by John Wiley & Sons, Inc.

Rosen and Goldsmith, "Systematic Analysis of Surface–Active Agents", vol. 12, pp 486–494, (1972) published by Wiley–Interscience, Inc.

Pharmaceutical Sciences by Remington, 17th Ed., Ch. 21, pp 324, (1985) published by Mark Publishing, Co.

J.Am. Pharm. Assoc., vol. 48, pp 451–459 (1959) and ibid., vol. 49, pp. 82–84 1960.

*Primary Examiner*—James M. Spear
(74) *Attorney, Agent, or Firm*—Robert R. Neller

(57) ABSTRACT

A dosage form is disclosed comprising means for delivering essentially a total dose of drug.

6 Claims, 8 Drawing Sheets

DOSAGE FORM COMPRISING MEANS FOR CHANGING DRUG DELIVERY SHAPE

CROSS-REFERENCE TO RELATED APPLICATION

This application claims the benefits of provisional application U.S. Ser. No. 60/058,323 filed Sep. 9, 1997 under 35 U.S.C. §119(e).

FIELD OF THE INVENTION

This invention pertains to both a novel and to a useful dosage form. Particularly, the invention relates to a dosage form capable of changing its shape. More particularly, the invention concerns a dosage form comprising a drug and means that respond to a physical-chemical influence, whereby the dosage form changes from an initial to a total drug delivery shape.

BACKGROUND OF THE INVENTION

Dosage forms, and more particularly osmotic dosage forms were disclosed by Theeuwes and Higuchi in U.S. Pat. Nos. 3,845,770 and 3,916,899. The dosage forms disclosed in these patents comprise a wall that surround a therapeutic drug. The wall is permeable to the passage of an external fluid, and it is substantially impermeable to the passage of drug. The dosage forms comprise a passageway through the wall for delivering the drug from the dosage form. These dosage forms release the drug by fluid being imbibed through the wall into the dosage form at a rate determined by the permeability of the wall and the osmotic pressure gradient across the wall. The dosage form thereby produces an aqueous solution containing the drug that is dispensed through the passage way from the dosage form. These dosage forms are effective extraordinarily for delivering a drug that is soluble in fluid and exhibits an osmotic pressure gradient across the wall against an external fluid.

A pioneer advancement in dosage forms was presented to the pharmaceutical-dispensing arts by inventor Theeuwes in U.S. Pat. No. 4,111,202. In this patent, the delivery kinetics of the osmotic dosage form is enhanced for delivering a drug that is insoluble to very soluble in fluid, by manufacturing the dosage form with a drug compartment and a displacement compartment separated by a piston. The piston is movable from a first rested to a second rested state. The osmotic dosage form delivers the drug by fluid imbibed through the wall of the dosage form into the displacement compartment thereby producing a solution that acts as a driving force that is applied against the piston. This force urges the piston to move against the drug compartment and correspondingly displace the drug through a passageway from the dosage form. While this dosage form operates successfully for its intended use, and while it can deliver many drugs of varying solubilities, its use can be limited, because of the complex manufacturing steps and the high cost needed for fabricating and placing the piston in the dosage form.

In U.S. Pat. No. 4,327,725 patentees Cortese and Theeuwes provided an osmotic dosage form for delivering a therapeutic agent that because of its solubility in aqueous and biological fluids, is difficult to deliver in therapeutic doses at a controlled rate over time. The dosage form of this patent comprises a wall that is semipermeable. The semipermeable wall surrounds a compartment containing a therapeutic agent that is insoluble to very soluble in aqueous and biological fluids and a separate osmogel. In operation, the osmogel, a hydrogel, expands in the presence of external fluid that enters the dosage form thereby causing the beneficial agent to be dispensed through a passageway from the dosage form. This dosage form operates successfully for its intended use, and it delivers many difficult to deliver therapeutic agents for their intended therapy.

Now, it has been observed unexpectedly, the above presented dosage forms may not deliver their intended dose of therapeutic agent, including a drug. This observation that these dosage forms may not achieve their full delivery potential is attributed to limitations in the prior art dosage forms. For instance, the dosage forms may not deliver all of the needed dose, and the prior art sought to compensate for this inherent limitation by manufacturing the dosage form containing an over dose of drug. This over dose or excess dose, often became trapped in the dosage form, or it led to dose dumping of the drug. The dose dumping is accompanied by over medication that may give rise to unwanted side effects. Then too, an osmogel in the dosage form may be restricted from its maximum expansion for displacing a drug from the dosage form due to the rigidity or lack of flexibility of the membrane of the dosage form.

It will be appreciated by those versed in the drug dispensing art, that if a dosage from can be provided that delivers all of its intended dose, substantially free of a over dose of drug, such a dosage form would have a positive value and also represent an advancement in the dispensing art. Likewise, it will be appreciated by those versed in the dispensing art, that if a novel dosage form is made available possessing physical properties for delivering a prescribed need dose of drug substantially-free of drug overage, the novel dosage form would find an immediate and practical application in the fields of pharmacy and medicine.

OBJECTS OF THE INVENTION

Accordingly, in view of the above presentation, it is an immediate object of this invention to provide a novel and nonobvious dosage form that represents an improvement and an advancement in the dispensing arts.

Another object of the invention is to provide an osmotic system manufactured as a dosage form that overcomes the disadvantages and limitations associated with the prior art dosage forms.

Another object of the invention is to make available a dosage form that delivers the required and needed dose of drug for accepted therapy free of delivering an overage of drug.

Another object of the invention is to provide a dosage form that keeps its physical integrity while delivering a therapeutic dose of drug while avoiding and/or reducing the risks associated with dose dumping of the drug.

Another object of the invention is to provide a dosage form comprising means for changing from a rested state to a flexible state and can deliver a dose of drug at a controlled-rate over a sustained release period of time.

Another object of the invention is to provide a new and useful dosage form that attains a zero-order release drug delivery profile while administering a drug to a human patient.

Another object of the invention is to make available a dosage form which dosage form during a drug delivery period is free from fractures and thereby avoids delivering a full dose of drug plus any drug overages in a shorter than the desired delivery time.

Another object of the invention is to provide a dosage form comprising a membrane that is flexible and thereby enable the dosage form to change its shape and thereby deliver essentially its total content of drug.

Another object of the invention is to provide a dosage form comprising a membrane endowed with a high concentration of plasticizer that enables the membrane to undergo change from a fixed, rigid non-rounded shape to a flexible rounded shape and thereby enhance the delivery of drug from the dosage form.

Another object of the invention is to provide a osmotic delivery system manufactured as a dosage form that can administer a complete pharmaceutical dosage regimen at a controlled rate and at a sustained-release rate for a particular time period, the use of which requires intervention only for the initiation and possible termination of the regimen.

Other objects, features, aspects and advantages of the invention will be more apparent to those skilled in the dispensing art from the following detailed specification taken in conjunction with the accompanying figures and accompanying claims.

BRIEF DESCRIPTION OF DRAWINGS

In the drawings, which are not drawn to scale, but are set forth to illustrate various embodiments of the invention, the drawing figures are as follows.

Drawing

Drawing

Drawing

Drawing

Drawing

Drawing

Drawing

Drawing

In the drawings and in the specification like parts in related figures are identified by like numbers. The terms appearing earlier in the specification and in the description of the drawings, as well as embodiments thereof, are further described elsewhere in the disclosure.

DETAILED DESCRIPTION OF DRAWINGS

Figure 1:
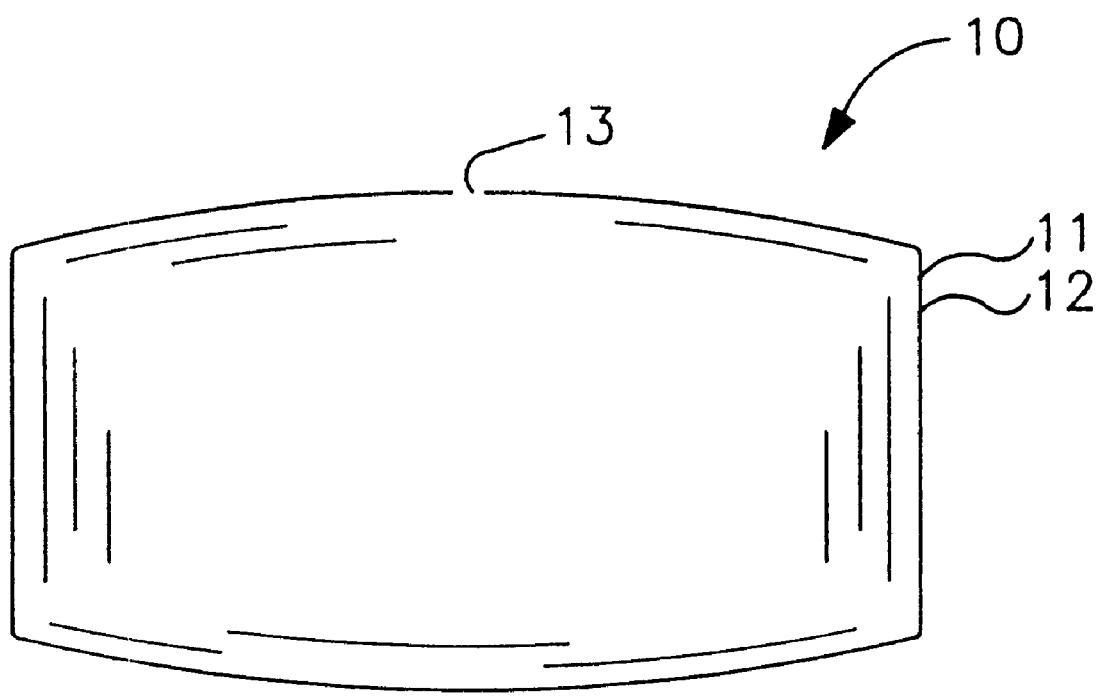
FIG. 1 is a view of a dosage form provided by the invention for orally administering a therapeutic agent to the gastrointestinal tract of a human.

Turning now to the drawing figures, which drawing figures are examples of the dosage forms provided by this invention, and which examples are not to be construed as limiting the invention, one example of the dosage form is illustrated in drawing FIG. 1 and designated by the numeral 10. In drawing FIG. 1, dosage form 10 comprises a body member 11 comprising membrane 12 that surrounds and encloses an internal compartment, not seen in drawing FIG. 1. Membrane 12 of dosage form 10 comprises an exit 13 for connecting the interior of dosage form 10 with the exterior environment of dosage form 10. The dosage form 10 of drawing FIG. 1 illustrates a controlled-release dosage form that delivers a therapeutic agent including a drug over an extended time. The dosage form comprising the controlled-release properties provided by this invention is successful at maintaining therapeutic drug levels in blood or in body tissue. The terms blood and body tissue refer to human patients, zoo and farm animals. The dosage form provided by this invention makes available to the practice of medicine continuous-release, extended-release therapy. The phrase extended release embraces sustained-release and prolonged-release over up to a single day of therapy. The extended, prolonged and sustained-release denotes a duration of drug delivery time over that achieved by conventional drug delivery forms such as tablets and capsules.

Figure 2:
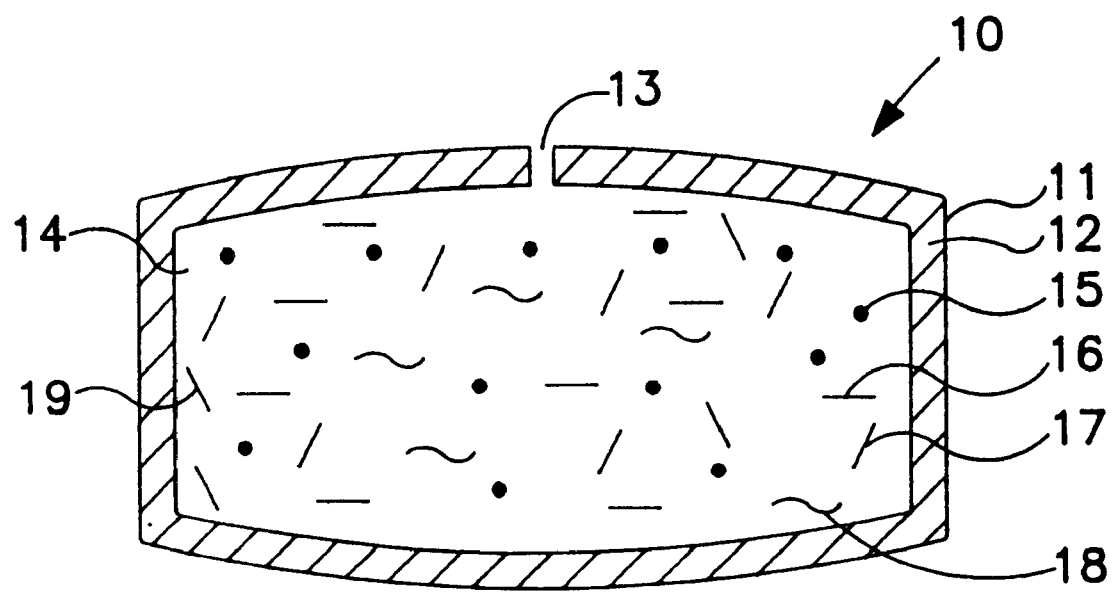
FIG. 2 is an opened view of the dosage form of drawing FIG. 1 for illustrating the structure of the dosage form.

In drawing FIG. 2, dosage form 10, manufactured as an osmotic dosage form, is seen in opened section. In drawing FIG. 2, dosage form 10 comprises body 11, membrane 12, that surrounds and defines an internal compartment 14. Membrane 12 comprises at least one exit means 13 that connects compartment 14 with the exterior of dosage form 10. Dosage form 10 can comprise more than one exit means 13.

Membrane 12 of dosage form 10, comprises a composition that is permeable to the passage of an exterior fluid present in a fluid environment of use, including the fluid of the gastrointestinal tract, and, membrane 12 is impermeable to the passage of a therapeutic agent and other components in compartment 14. The composition comprising membrane 12 is semipermeable, it is nontoxic, inert, flexible, exhibits plasticity, the ability to change shape in response to applied pressure, and is pharmaceutically acceptable for delivering a therapeutic agent to an environment of use including an animal and a human patient.

Membrane 12, in one manufacture comprises a membrane-forming composition comprising a member selected from the group consisting of a cellulose ester polymer, a cellulose ether polymer and a cellulose ester-ether polymer. These cellulosic polymers have a degree of substitution, DS on the anhydroglucose unit, from greater than 0 up to 3 inclusive. By "degree of substitution" is meant the average number of hydroxyl groups originally present on the anhydroglucose unit comprising the cellulose polymer that are replaced by a substituting group. Representative membrane 12 polymers comprise a member selected from the group consisting of cellulose acylate, cellulose diacylate, cellulose triacylate, cellulose acetate, cellulose diacetate, cellulose triacetate, mono-, di- and tricellulose alkanylates, mono-, di- and tricellulose alkenylates, mono-, di-, and tricellulose alkinylates and mono-, di- and tricellulose aroylates. Exemplary polymers include cellulose acetate having a DS of up to 1 and an acetyl content of up to 31%; cellulose acetate having a DS of 1 to 2 and any acetyl content of 21 to 35%; cellulose acetate having a DS of 2 to 3 and an acetyl content of 35 to 44.8%; and the like. More specific cellulosic polymers comprise cellulose propionate having a DS of 1.8, a propyl content of 39.2 to 45% and a hydroxyl content of 2.8 to 5.4; cellulose acetate butyrate having a DS of 1.8, an acetyl content of 13 to 15% and a butyryl content of 34 to 39%; cellulose acetate butyrate having a acetyl content of 2 to 29%, a butyryl content of 17% to 53% and a hydroxyl content of 0.5 to 4.7; cellulose triacylates having a DS of 2.9 to 3, such as cellulose trivalerate, cellulose trilaurate, cellulose tripalmitate, cellulose trisuccinate and cellulose trioctanoate; celluloses diacylate having a DS of 2.2 to 2.6, such as cellulose disuccinate, cellulose dipalmitate, cellulose dioctanoate, cellulose dipentanoate, co-esters of cellulose, such as cellulose acetate butyrate, and cellulose acetate propionate.

Additional semipermeable polymers for providing membrane 12 comprise ethyl acrylate methylmethacrylate copolymers; acetaldehyde dimethylcellulose acetate; cellulose acetate ethylcarbamate; cellulose acetate methycarbamate; cellulose diacetate propylcarbamate; cellulose acetate diethylaminoacetate; semipermeable polyamide; semipermeable polyurethane; semipermeable sulfonated polystyrene; semipermeable crosslinked selective polymer formed by the coprecipitation of a polyanion and polycation, as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132, semipermeable, lightly crosslinked polystyrenes; semipermeable crosslinked poly(sodium styrene sulfonate); semipermeable crosslinked poly(vinylbenzyltrimethyl ammonium chloride); and semi-permeable polymers possessing a fluid permeability of $2.5 \times 10^8$ to $5 \times 10^2$ ($cm^2$/hr·atm), expressed per atmosphere of hydrostatic or osmotic pressure difference across the semipermeable wall. The polymers are known to the polymer art in U.S. Pat. Nos. 3,845,770, 3,916,899 and 4,160,020; and in *Handbook of Common Polymers*, Scott, J. R. and W. J. Roff, 1971, CRC Press, Cleveland, Ohio. Membrane 12 comprises 35 wt % to 60 wt % of the semipermeable, pharmaceutically acceptable polymer.

Membrane 12 comprises a plasticizer that make membrane softer, flexible, distensible, and compatible with the ingredients comprising membrane 12. Representative of plasticizers useful for the plasticization of membrane 12, comprise adipic acid plasticizers, azelaic acid plasticizers, benzoic acid plasticizers, citric acid plasticizers, epoxy plasticizers, glycol plasticizers, glycerols, phosphoric acid plasticizers, phthalic acid plasticizers, ricinoleic acid plasticizers, sebacic acid plasticizers, and trimellitic acid plasticizers. Examples of specific plasticizers comprise a member selected from the group consisting of monoacetin, diacetin, triacetin, glycerine, polyethylene glycol, di-n-hexyl adipate, bio (2-ethylhexyl) adipate, bio (2-ethylhexyl) azelate, diethylene glycol dibenzoate, tri-n-butyl citrate, tri-n-butyl acetylcitrate, epoxidized soy oil, diethylene glycol dipelargonate, triethylene glycol di (2-ethylbutyrate), tri (2-ethylhexyl) phosphate, 2-ethylhexyl diphenyl phosphate, dibutyl phthalate, dinonyl phthalate, diphenyl phthalate, n-butyl acetyl ricinoleate, di-n-butyl sebacate, bio (2-ethylhexyl) terphthelate, trio (2-ethylhexyl) trimellitate, and trisisodecyl trimellitate. The concentration of a plasticizer in membrane 12 is 15 wt % to 55 wt %. The plasticizers are known in the art in Encyclopedia of Polymer Science and Engineering, Supplement Volume, Acid-Base Interactions to Vinyl Chloride Polymers, pp 568–573, (1989), published by John Wiley & Sons, Inc.

Membrane 12 of dosage form 10 comprising the semipermeable polymer and the plasticizer also comprises a pharmaceutically acceptable surfactant. The surfactant for the purpose of this invention is amphiphilic as it contains both a hydrophobic and a hydrophilic group. Representative of surfactants that exhibit solubility in aqueous and non-aqueous solvents are polyoxyethylene fatty acid esters that includes polyoxyethylene monostearate, polyoxyethylene sorbitan monopalmitate, polyoxypropylene glycols that include polyoxypropylene glycol having a molecular weight of 950 and 3 moles to 85 moles of ethylene oxide, polyoxypropylene glycol possessing a molecular weight of 1200 and 7 to 40 moles of ethylene glycol, polyoxypropylene glycol possessing a molecular weight of 1750 and 5 moles to 160 moles of ethylene oxide, polyoxypropylene glycol having a molecular weight of 2050 and 10 moles to 110 moles of ethylene oxide, polyoxy-propylene glycol having a 2250 molecular weight and 5 moles to 200 moles of ethylene oxide, polyoxypropylene glycol possessing a molecular weight of 2750 and 15 to 250 moles of ethylene oxide, and polyoxypropylene glycol of 3250 molecular weight with 8 moles to 300 moles of ethylene glycol. The amount of surfactant in membrane 12 is 0.5 wt % to 40 wt %. The surfactants are known in *Systematic Analysis of Surface-Active Agents*, by Rosen and Goldsmith, Vol. 12, pp 486–494, (1972) published by Wiley-Interscience, Inc. The surfactants known as Myrij® and Tween®) are commercially available from the JCI Americas, Inc., Wilmington, Del. The Pluronic® surfactants are available from BASF Corp., Mt. Olive, N.J. Additional surfactants that can be used for the purpose of this invention are surfactants possessing a hydrophilic-lyophilic balance of 6 to 40 as represented by polyoxyethylene monostearate with a hydrophilic-lipophilic balance (HLB) of 11.1, trolamine (HLB) of 12, and polyoxyethylene lauryl ether with (HLB) of 16.9. The hydrophilic-lipophilic balance of surfactants are known in Pharmaceutical Sciences by Remington, 17$^{th}$ Ed., Ch. 21, pp 324,(1985) published by Mark Publishing, Co.

Dosage form 10, when manufactured as an osmotic dosage form with controlled-release properties comprises at least one exit 13 in the dosage form membrane 12. The phase controlled-release as used herein, indicates that control is exercised over both the duration and the profile of the drug-release pattern. The expression passageway 13, as used for the purpose of this invention, includes aperture, orifice, bore, pore, porous element through which the drug can be pumped, diffuse, travel or migrate, a hollow fiber, capillary tube, porous overlay, porous insert, microporous member, and porous composition. The expression also includes a compound that erodes or is leached from the membrane in the fluid environment of use to produce at least one passageway in dosage form. Representative compounds suitable for forming at least one passageway, or a multiplicity of passageways, includes an erodible poly(glycolic) acid or poly(lactic) acid member in the membrane; a gelatinous filament; a water-removable poly(vinyl alcohol); leachable compounds such as fluid removable pore-forming polysaccharides, acid, salts, or oxides. A passageway or a plurality of passageways can be formed by a leaching a compound such as sorbitol, sucrose, lactose, fructose, or the like, from the membrane to provide a controlled-release dimensioned pore-passageway. The passageway can have any shape such as round, triangular, square, elliptical, and the like, for assisting in the controlled-metered release of drug from dosage form. Dosage form can be constructed with one or more passageways in spaced-apart relation on one or more surfaces of a dosage form. Passageway and equipment for forming passageways are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled releasing dimension, sized, shaped and adapted as a releasing-pore formed by aqueous leaching to provide a drug releasing-pore formed by aqueous leaching to provide a releasing-pore of controlled release-rate are disclosed in U.S. Pat. No. 4,200,098 by Ayer and Theeuwes; and in U.S. Pat. No. 4,285,987 by Ayer and Theeuwes.

Dosage form 10 comprises in compartment 14 a therapeutic agent 15, represented by dots. The phrase therapeutic agent 15 as used herein includes medicines or drugs, nutrients, vitamins, food supplements, and other beneficial agents that provide a therapeutic or a health benefit to animals, including a warm-blooded animal, humans, farm animals and zoo animals. The term drug includes any physiologically or pharmacologically active substance that produces a local or a systemic effect in a host. The drug that can be delivered includes drug that act on the central nervous system, depressants, hypnotics, sedatives, tranquilizers, muscle relaxants, analgesics, anesthetics, hormones, contraceptives, sympathomimetics, diuretics, antiparasites, hypoglycemics, ophthalmics, and cardiovascular drugs. Representative of drug 15 comprises vancomycin, valoxifene, cyclosporin, lisinopril, ondansetron, fluvoxamine, captopril, phentolamine, enalapril, amisulpride, imipramine, carbamazepine, famciclovir, clomipramine, penciclovir, pergolide, mesalazine, enitabas, talviraline, clozapine, nevirapine, zidoviudine, ganciclovir alendronic, imiquimod, naratriptan, sparflozacin, lamivudine, zidovudine, omeprazole, aiclovir, valaceclovir, oxcarbazepine, ganciclovir, amfebutamonc, cidofovir, doxazosin, ebastine, formoterol, moexipril, penciclovir, sertraline, spirapril, fenfluramine, dexfenfluramine, phentermine, fenphen, oxybutynin, felodipene, metoprolol, saquinavir, ritonavir, indinavir, and nelfinavir. The dose of drug in dosage form 10 is 0.5 mg to 650 mg.

Drug 15 can be in various forms, such as uncharged molecules, molecular complexes, pharmaceutically acceptable salts including hydrochloride, hydrobromide, sulfate, laurylate, palmitate, phosphate, nitrate, nitrite, borate, acetate, maleate, tartrate, oleate, and salicylate. For acid drugs, salts of metals, amines, or organic cations, for example, quaternary ammonium can be used for the operative drug. Derivatives of drugs, such as esters, ethers, and amides can be used for administering a drug. A drug that is water insoluble can be used in a form that is a water soluble derivative thereof as a solute, and on its delivery is converted by enzymes, or hydrolyzed by the body pH, or by other metabolic processes to the original pharmaceutically active form.

Compartment 14 contains a pharmaceutically acceptable osmopolymer carrier 16 that aids in transporting drug 15 from the dosage form. The osmopolymer 16, represented by dashes, is homogeneously blended with drug 15. The osmopolymers comprise a member selected from the group consisting of a polyalkylene oxide possessing a 75,000 to 600,000 weight-average molecular weight, or a carboxyalkylcellulose possessing a 25,000 to 150,000 weight-average molecular weight. Representative of polyalkylene oxide comprises polyethylene oxide of 100,000 molecular weight, polyethylene oxide of 200,000 molecular weight, polyethylene oxide of 300,000 molecular weight, polypropylene oxide of 400,000 molecular weight, and polypropylene oxide of 600,000 molecular weight. Representative of carboxyalkylcellulose comprise a member selected from the group consisting of alkali carboxyalkylcellulose, sodium or potassium carboxymethylcellulose of 40,000 molecular weight, lithium, or sodium or potassium carboxymethylcellulose of 75,000 molecular weight, sodium carboxymethylcellulose of 90,000 molecular weight, and potassium carboxy-ethylcellulose of 125,000 molecular weight. The dosage form comprises 20 wt % to 100 wt % of osmopolymer 16.

The therapeutic composition in dosage form 10 comprises a hydroxy-propylalkylcellulose 17 that imparts cohesive qualities to the therapeutic composition comprising drug 15 and osmopolymer 16. The binder imparts a cohesiveness to the composition during manufacture and when an external fluid enters dosage form 10 the binder improves the free-flowing qualities of the composition for administration to a human patient. Representative of hydroxypropylalkylcellulose possessing a 9,000 to 400,000 number-average molecular weight comprise a member selected from the group consisting of hydroxypropylmethylcellulose, hydroxypropylethylcellulose, hydroxypropylisopropylcellulose, hydroxypropylbutylcellulose, and hydroxypropylpentyl-cellulose. Representative of additional materials that can be used as binders for the purpose of this invention comprise a member selected from the group consisting of starch, gelatin, molasses and polyvinylpyrrolidone. The amount of binder in the therapeutic composition in drawing FIG. 2 is 0.5 wt % to 10 wt %.

The therapeutic composition comprises a lubricant 18 used during the manufacture of the therapeutic composition to prevent or reduce adhesion of the composition to the surfaces of dies and punches. The lubricants comprise a member selected from the group consisting of calcium stearate, zinc stearate, magnesium stearate, magnesium oleate, calcium palmitate, sodium suberate, potassium laureate, stearic acid, salts of fatty acids, salts of alicyclic acid, salts of aromatic acids, oleic acid, palmitic acid and a mixture of a salt of a fatty, alicyclic or aromatic acid. The amount of lubricant in a therapeutic composition is 0.01 wt % to 3.0 wt %.

The therapeutic composition can comprise 0 wt % to 3 wt % of a colorant 19. The colorant 19 makes the dosage form more esthetic in appearance and it serves to identify the dosage form during manufacture and in therapy. The colorants are represented by FD&C Red No. 3; FD&C Red No. 40; FD&C Yellow No. 5; FD&C Yellow No. 6; FD&C Blue No. 1; FD&C Blue No. 2; FD&C Green No. 3; and iron oxide. The concentration of all ingredients in a composition is equal to 100 wt %.

Figure 3:
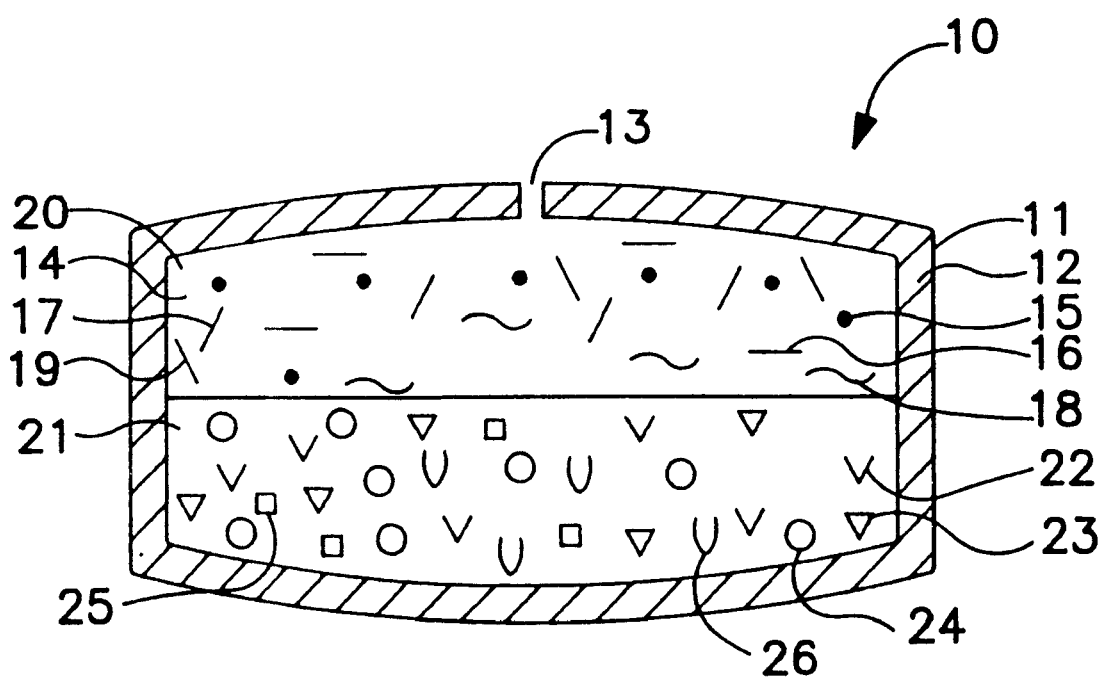
FIG. 3 is an opened view of the dosage form of drawing FIG. 1 illustrating the structure of a different dosage form provided by the invention for delivering a drug to an environment of use comprising a fluid.

In drawing FIG. 3, dosage form 10 is seen in opened view for illustrating the internal compartment 14. In drawing FIG. 3, dosage form 10 comprises body member 11, membrane 12, exit 13 and internal compartment 14. Internal compartment comprises the therapeutic composition, which can be identified also as therapeutic layer 20 comprising drug 15, osmopolymer carrier 16, cohesive binder 17, lubricant 18, and colorant 19, as described above in drawing FIG. 2. In drawing FIG. 3, dosage form 10 comprises a displacement composition 21, also identified as expandable layer 21. Displacement layer 21 comprises an expandable osmopolymer 22, represent by V. The osmopolyer 22 comprises an osmopolymer having a greater number molecular weight than the osmopolymer in the therapeutic composition. The displacement layer 21 comprises a member selected from the group consisting of polyalkylene oxide of 1,000,000 to 10,000,000 weight-average molecular weight. Representative of polyalkylene oxides are polyethylene oxide of I million molecular weight, polyethylene oxide of 2 million molecular weight, polypropylene oxide of 4 million molecular weight, polyethylene oxide of 5 million molecular weight, and polyethylene oxide of 7.5 million molecular weight. The osmopolymer 22 includes carboxyalkylcellulose of 200,000 to 3,250,000 molecular weight-average molecular weight. Representative of carboxyalkylcellulose comprises a member selected from the group consisting of lithium carboxymethylcellulose, potassium carboxymethylcellulose of 200,000 molecular weight, sodium carboxymethylcellulose of 200,000 molecular weight, sodium carboxymethyl-cellulose of 1,250,000 molecular weight, potassium carboxymethylcellulose of 1,500,000 molecular weight, sodium carboxyethylcellulose of 2,250,000 molecular weight, and sodium carboxymethylcellulose of 3,250,000 molecular weight. The osmopolymer 22, also known as hydrogel or osmogel, exhibit the ability to imbibe fluid and expand as a result of their osmotic pressure gradient across membrane 12. The osmopolymer expands, pushes, and displaces the therapeutic composition through exit 13 from dosage form 10. The amount of osmopolymer 22 in layer 21 is 40 wt % to 75 wt %.

Displacement, expandable layer 21 comprises 10 wt % to 40 wt % of an osmagent 23, represented by a triangle. The osmagent 23 are known as osmotically active compound and osmotically active solute. The osmagent exhibits an osmotic pressure gradient across membrane 12, imbibes fluid into dosage form 10 that aids osmopolymer 21 to expand and displace the therapeutic composition from dosage form 10. Representative of osmagent 23 comprise a member selected from the group consisting of sodium chloride, potassium chloride, magnesium sulfate, lithium chloride, lithium phosphate, sodium phosphate, potassium sulfate, potassium sulfite, sodium sulfate, sodium sulfate, potassium nitrate, and potassium phosphate.

Displacement layer 21 comprises a binder 24. Representative of binder 24 comprise a member selected from the group consisting of hydroxyalkylcellulose, hydroxypropyl celluloses, hydroxypropylalkylcelluloses and polyvinyls. The hydroxypropylalkylcellulose possess a 9,000 to 400,000 number-average molecular weight comprising a member selected from the group consisting of hydroxypropylmethylcellulose, hydroxpropylethylcellulose, hydroxypropylbutylcellulose, hydroxypropylpentylcellulose, and hydroxypropylhexylcellulose. The polyvinyls of 1,200 to 360,000 viscosity-average molecular weight comprising, a member selected from the group consisting of polyvinylpyrrolidone, polyvinylcarbazole, polyvinylpyridine, polyvinyloxazole, polyvinylmethyloxa-zolidone, polyvinylbutyrol, polyvinylacetate, polyvinylalcohol, copolymer of polyvinylprrolidone with vinyl acetate, copolymer of polyvinylpyrrolidone and vinyl alcohol, copolymer of polyvinylpyrrolidone with vinyl chloride, copolymer of polyvinylpyrrolidone with vinyl fluoride, copolymer of polyvinylpyrrolidone with vinyl butyrate, copolymer of polyvinylpyrrolidone with vinyl laurate, and copolymer of polyvinylpyrrolidone with vinyl stearate. The amount of binder in the displacement composition is 0.5 wt % to 15 wt %.

Displacement layer 21 comprises 0 wt % to 2.75 wt % of a colorant 25. The colorants are nontoxic and include Food and Drug Administration colorants such as FD&C No. 1 blue, ferric oxide, and the colorants disclosed above. Displacement layer 21 comprises 0.05 wt % to 3.75 wt % of a lubricant 26. The lubricant comprises a member selected from the group consisting of sodium stearate, potassium stearate, magnesium stearate, stearic acid, calcium stearate, calcium palmitate, potassium oleate, and the lubricants presented above. The concentration of the ingredients in layer 21 is 100 wt %.

Figure 4:
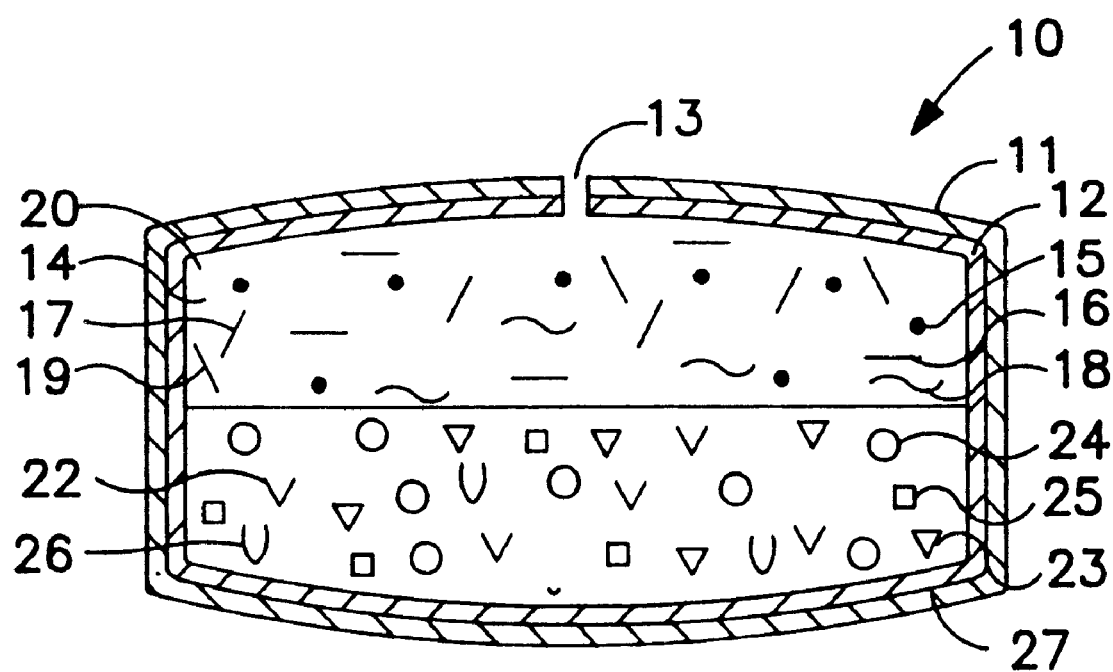
FIG. 4 is a view of a dosage form made available by the invention wherein the dosage form comprises an inner subcoat membrane and an outer overcoat membrane.

Drawing FIG. 4 depicts another dosage form 10 made available by the present invention. In drawing FIG. 4, dosage form 10 is seen in opened view comprising the structure, ingredients, and sustained-release rate programs presented accompanying drawing FIG. 2 and drawing FIG. 3. In drawing, FIG. 4, membrane 12 is defined as an inner subcoat or subcoat 12. Subcoat 12 is in laminated, contacting arrangement with overcoat 12 also identified as overcoat membrane 27. Overcoat membrane 27 comprises 60 wt % to 99.5 wt % of a hydroxypropylalkylcellulose possessing 9,000 to 400,000 number-average molecular weight. The hydroxypropylalkylcellulose polymers for manufacturing membrane 27 comprise a member selected from the group consisting of hydroxypropylmethylcellulose, hydroxypropylethyl-cellulose, hydroxypropylbutylcellulose, hydroxypropylpentylcellulose and hydroxypropylhexylcellulose. Membrane 27 compresses 0.5 wt % to 30 wt % of a polyethylene glycol. The polyethylene glycols possess a viscosity-average molecular weight of 200 to 20,000. The polyethylene glycols are neutral, hydrophilic polymers used to form membrane 27. The polyethylene glycol used to provide membrane 27 for this invention excludes polyethylene oxide. The polyethylene glycols are commercially available from Union Carbide Corporation.

Figure 5:
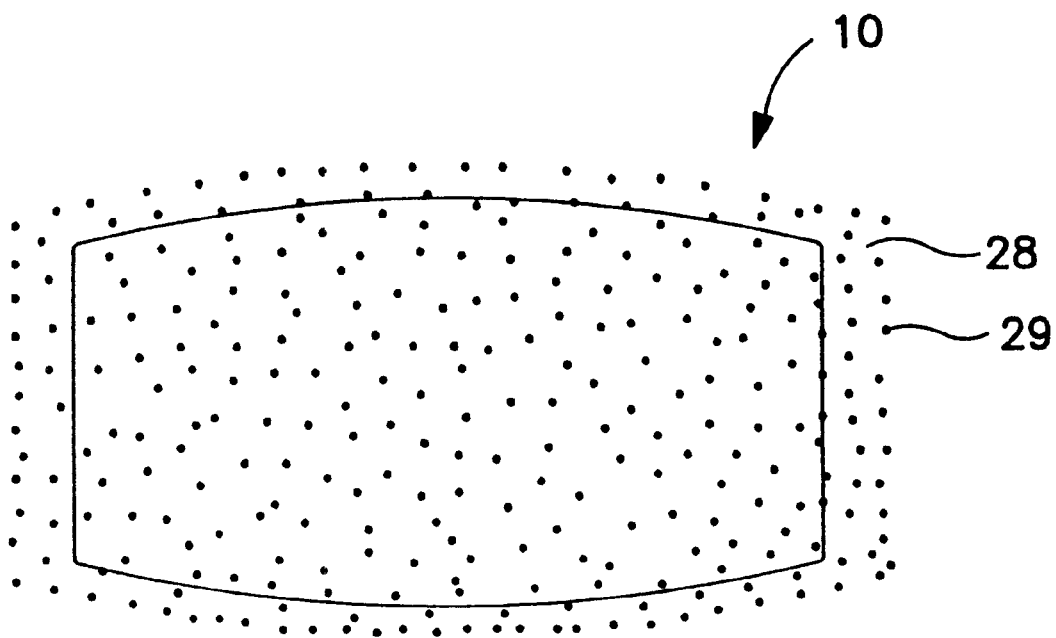
FIG. 5 is a view of a dosage form made available by the invention comprising an outermost overcoat of instant release therapeutic agent including a drug.

Dosage form 10 as seen in drawing FIG. 5 depicts another manufacture provided by this invention. Dosage form 10 comprises a therapeutic overcoat 28 on the outer surface, of dosage form 10. The therapeutic overcoat comprises 0.5 mg to 50 mg of a drug and a pharmaceutically acceptable carrier selected from the group consisting of alkylcellulose, hydroxyalkylcellulose, and hydroxypropylalkylcellulose. Representative of pharmaceutically acceptable carriers include methyl-cellulose, hydroxyethylcellulose, hydroxypropylmethylcellulose, hydroxypropylethylcellulose, and hydroxypropylbutylcellulose. Therapeutic overcoat 28 comprising drug 29 provides therapy immediately as therapeutic overcoat 28 dissolves, or undergoes dissolution in the presence of gastrointestinal fluid present in a human patient and concurrently therewith delivers drug 29 on entrance into the gastrointestinal tract for immediate drug 29 therapy.

Figure 6:
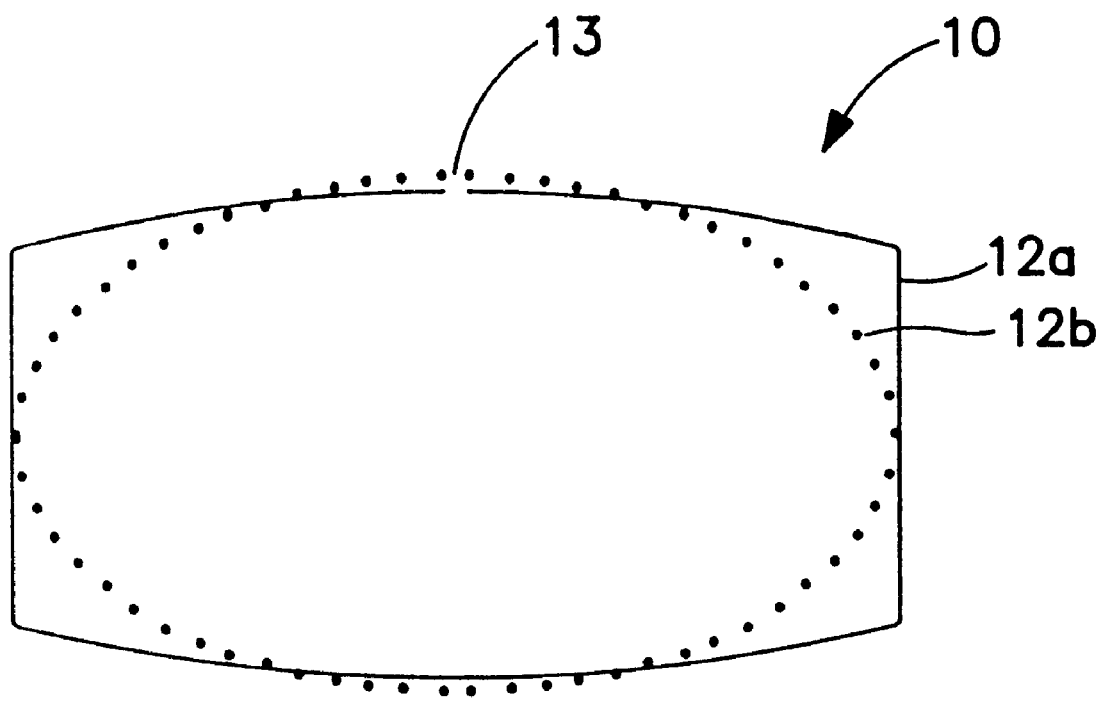
FIG. 6 depicts a dosage form made available by the invention, which dosage form during its therapeutic agent operation changed from a first original shape to a second expanded state.

Dosage form 10 in drawing FIG. 6 is seen in operation delivering the maximum dose of drug. In operation, as dosage form 10 enters a drug receiving environment, such as the gastrointestinal tract of a patient, the dosage form changes in shape from a first fixed state or shape 12a to a second different state or shape 12b. As dosage form 10 moves in gastrointestinal transit, plasticizer present in the membrane of the dosage form is slowly dissolved and/or leached from the membrane. Simultaneously therewith, fluid is imbibed into the dosage form generating hydration pressure in the dosage form thereby causing membrane 12a to change shape to membrane 12b. The dosage form becomes rounded and/or spherical, thereby permitting the dosage form to push more and/or all of its drug from the dosage form. As the dosage form's previously angled edges near the exit are rounded, drug flows more freely as afforded by the rounded membrane with less drug maintained or trapped inside the dosage form. Thus, this in vivo operation assures the delivery of a maximum dose of drug.

PROCESS FOR PROVIDING THE INVENTION

The membrane of the dosage form can be formed by using the air suspension procedure. This procedure consists in suspending and tumbling the composition in a current of air and membrane-forming composition until a membrane is applied to the drug forming compartment. The air suspension procedure is well suited for independently forming the membrane. The air suspension procedure is described in U.S. Pat. No. 2,799,241; *J. Am. Pharm. Assoc.*, Vol. 48, pp. 451–459 (1959); and *ibid.*, Vol. 49, pp. 82–84 (1960). The membrane can be formed with a membrane-forming composition in a Wurster® air suspension coater using an organic solvent, such as acetone-water cosolvent 90:10 (wt;wt) with 2.5 wt % to 7 wt % polymer solids. An Aeromatic® air suspension coater using, for example, a methylenedi-chloride methanol cosolvent comprising 87:13 (v.v) can be used for applying the membrane. Other membrane-forming techniques, such as pan coating, can be used for providing the dosage form. In the pan coating system membrane-forming compositions are deposited by successive spraying of the composition or the bilayered arrangement, accompanied by tumbling in a rotating pan. A larger volume of cosolvent can be used to reduce the concentration of polymer solids to produce a thinner wall. Finally, the membrane of the coated compartments are laser or mechanically drilled, and then dried in a forced air or humidity over for 1 to 3 days or longer to free the solvent. Generally, the walls formed by these techniques have a thickness of 2 to 20 mils (0.051 to 0.510 mm) with a preferred thickness of 2 to 6 mils (0.051 to 0.150 mm).

The dosage form of the invention in another embodiment is manufactured by standard manufacturing techniques. For example, in one manufacture the beneficial drug and other ingredients comprising a therapeutic composition or forming the first layer facing the exit means are blended, or the ingredients are blended then pressed, into a solid layer. The drug and other ingredients can be blended with a solvent and formed into a solid or semisolid formed by conventional methods such as ball-milling, calendering, stirring or roll-milling and then pressed into a selected shape. The drug layer possesses dimensions that correspond to the internal dimensions of the area the drug layer is to occupy in the dosage from. Next, the drug layer is placed in contact with the displacement layer. The layering of the drug layer and the displacement layer can be fabricated by conventional press-layering techniques. The bilayers possess dimensions corresponding to the dimensions of the internal compartment or the dosage form. Finally, the two-layer compartment forming members are surrounded and coated with an outer membrane. A passageway is laser drilled or mechanically drilled through the membrane to contact the drug layer, with the dosage form optically-oriented automatically by the laser equipment for forming the passageway on the preselected drug surface.

In another manufacture, the dosage from is manufactured by the wet granulation technique. In the wet granulation technique the drug and the ingredients comprising the first layer are blended using an organic or inorganic solvent, such as isopropyl alcohol-methylene dichloride 80:20 (v.v) as the granulation fluid. Other granulating fluid, such as water, isopropyl alcohol, or denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the in the blender. The granulating fluid is added until a wet blend mass is produced, which wet mass is then forced through a 20 mesh screen onto over trays. The blend is dried for 18 to 24 hours at 25° C. to 40° C. The dry granules are then screened with a 16 mesh screen. Next, a lubricant is passed through a 60 mesh screen and added to the dry screened granule blend. The granulation is put into milling jars and mixed on a jar mill for 2 to 10 minutes. The first and second layered compositions are pressed into a layered tablet, for example, in a Manesty® layer press.

Another manufacturing process that can be used for providing the drug and displacement compositions comprise blending their powdered ingredients in a fluid bed granulator. After the powdered ingredients are dry blended in the granulator, a granulating fluid, for example, poly(vinylpyrrolidone) in a solvent, such as in water, is sprayed and mixed with the respective powders. The powders are then dried in a granulator. This process is continued while spraying the granulating fluid. After the granules are dried, a lubricant, such as stearic acid or magnesium stearate, is blended as above into the mixture. The granules are then pressed in the manner described above. In another embodiment, when the fluid be granulating process is used to manufacture the displacement layer, an antioxidant present in the polyalkylene oxide can be removed during the processing step. If antioxidant is desired, it can be added to the displacement layer, this can be accomplished during the fluid bed granulation described above.

The dosage form of this invention is manufactured in another embodiment by mixing a drug with composition-forming ingredients and pressing the composition into a solid layer possessing dimensions that correspond to the internal dimensions of the compartment space adjacent to a passageway. In another embodiment, the drug and other drug composition forming ingredients and a solvent are mixed into a solid, or semi-solid, by conventional methods such as ball-milling, calendering, stirring, or roll-milling, and then pressed into a preselected, layer-forming shape.

In the manufactures as presented above, the manufacture comprising a drug and an osmopolymer or osmagent are placed in contact with the displacement layer, and the two layers are surrounded with a semipermeable membrane. The layering of the drug composition and the second displacement composition can be accomplished by using a conventional two-layer tablet press technique. The membrane can be applied by molding, spraying or dipping the pressed shapes into wall-forming materials. Another technique that can be used for applying the membrane is the air-suspension coating procedure. This procedure consists in suspending and tumbling the two layers in a current of air until the membrane forming composition surrounds the layers. Manufacturing procedures are described in *Modern Plastics Encyclopedia*. Vol. 46, pp. 62–70 (1969); and in *Pharmaceutical Sciences*, by Remington, 14$^{th}$ Ed., pp.1626–1979 (1970) published by Mack Publishing Co., Easton, Pa. The dosage form can be manufactured by following the teaching the U.S. Pat. Nos. 4,327,725; 4,612,008; 4,783,337; 4,863,456; and 4,902,514.

Exemplary solvents suitable for manufacturing the membrane, the composition layers and the dosage from include inert inorganic and organic solvents that do not adversely harm the materials, the wall, the layer, the composition and the drug. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone, alcohol, methanol, ethanol, isopropyl alcohol, butyl alcohol, methyl acetate, ethyl acetate, isopropyl n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, proplylene dichloride, chloroform, nitroethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures, such as acetone and water, acetone and methanol, acetone and ethyl alcohol, methylene dichloride and methanol, and ethylene dichloride and methanol.

DETAILED DISCLOSURE OF EXAMPLES

The following examples are merely illustrative of the present invention and they should not be considered as limiting the scope of the invention in any way, as these examples and other equivalents thereof will become apparent to those versed in the art in the light of the present disclosure and the accompanying claims.

EXAMPLE 1

An osmotic dosage form designed to deliver at controlled rate the calcium-channel blocker, nifedipine, for once a day treatment of angina and hypertension is fabricated according to this invention. The dosage form consists of a layered tablet which is coated with the specialized rate-controlling membrane that changes shape as it functions. The layer of the tablet consists of the active drug and other layer forming ingredients.

The drug layer of the dosage form is formulated by first micronizing 200 grams of the drug to a particle size of approximately 3–5 microns. Then, 745 grams of polyethylene oxide having a molecular weight of approximately 200,000 grams per mole, and 50 grams of hydroxypropylmethylcellulose having a hydroxypropyl content of 10 weight percent, a methoxyl content of 29 weight percent, and a molecular weight of 11,300 grams per mole, are passed through a sieve having 40 wires per inch. All the components are then dry mixed. To the mixture is added ethyl alcohol, anhydrous, with stirring until a uniformly damp mass is produced. The resulting mass is passed through a screen having 20 wires per inch. The resulting granules are then air dried overnight at room temperature. The dried granules are then passed through again a screen having 20 wires per inch. Finally, 5 grams of magnesium stearate, previously passed through a screen having 60 wires per inch, is tumble mixed into the dried granules. The resulting composition is compressed into tablets each weighing 150 mg.

The just prepared drug tablets are coated next with the rate-controlling membrane of this invention. The membrane formulation consisted of a subcoat and an overcoat. The subcoat formulation was prepared by first dissolving 12 grams of polyethylene glycol having a molecular weight of 400 grams per mole in 1760 grams of water. Then, 14.4 grams of polyoxy-ethylene (20) sorbitan tristearate was added with stirring while warming the fluid to 40 degrees centigrade. When the 40 degree temperature was reached, 105 grams of triacetin was added and the stirring rate was increased. The heat was turned off and the fluid was allowed to cool with stirring for one hour. Stirring was stopped and then the fluid was allowed to cool at room temperature. After standing overnight, the fluid was then stirred for 30 minutes. Then, 108 grams micronized cellulose acetate was slowly added to the vortex of the fluid until fully dispersed in the fluid. The cellulose acetate had a molecular weight of 40,000 grams per mole, an acetyl content 39.8 weight percent, and had been air jet milled to a nominal particle size of 5–10 microns. The resulting dispersion was mixed for one hour.

Next, the membrane composition is charged into a fluidized bed coater. Then, the batch of tablets is charged into the fluidized bed coater. The membrane composition fluid while being continuously stirred was applied by atomizing it through a standard nozzle with air pressure of 0.8 barr at a spray rate of 9 grams per minute. The bed of tablets was fluidized in a current of warm air with an air flow of 140–160 cubic feet per minute, an inlet temperature of 50–51 degrees centigrade, an outlet temperature of 33–34 degrees centigrade to reach a membrane thickness of 8 mils. Next, the just membrane coated tablets were transferred to a forced air oven thermostated at 50° C. for 4 days. Then, a single, round exit was drilled, (30 mils, 0.762 mm) through the membrane to connect the drug composition with the exterior of the dosage form for delivering at a sustained-release rate for its intended therapy.

EXAMPLE 2

The above procedure is repeated, except in this example the drug is a member selected from the group consisting of doxazosin, ebastine, fludarbine, formoterol, letrozle, lodoxamide moexipril, penciclovir, sertaline, sparfloxacin, and spirapril.

EXAMPLE 3

An osmotic dosage form designed to deliver at controlled rate the calcium-channel blocker, nifedipine, for once a day treatment of angina and hypertension is fabricated according to this invention. The dosage form consists of a two layer tablet which is coated with the invention's specialized rate-controlling membrane which changes shape as it functions. One layer of the tablet consists of the active drug and the other layer of the tablet consists of a push layer.

The drug layer is formulated by first by micronizing 200 grams of the drug to a particle size of approximately 3–5 microns. Then, 745 grams of polyethylene oxide having a molecular weight of approximately 200,000 grams per mole, and 50 grams of hydroxypropylmethylcellulose having a hydroxypropyl content of 10 weight percent, a methoxyl content of 29 weight percent, and a molecular weight of 11,300 grams per mole, are passed through a sieve having 40 wires per inch. All the components are then dry mixed. To the mixture is added ethyl alcohol, anhydrous, with stirring until a uniformly damp mass is produced. The resulting mass is passed through a screen having 20 wires per inch. The resulting granules are then air dried overnight at room temperature. The dried granules are then passed through again a screen having 20 wires per inch. Finally, 5 grams of magnesium stearate, previously passed through a screen having 60 wires per inch, is tumble mixed into the dried granules. The resulting composition is referred to as the drug layer granulation.

A displacement or push layer granulation is formed by passing 643 grams of polyethylene oxide having a molecular weight of 5 million, 292 grams of sodium chloride, 50 grams of hydroxpropylmethylcellulose having a hydroxypropyl content of 10 weight percent and a methoxyl content of 29 weight percent a molecular weight of 11,300 grams per mole, and 10 grams of red ferric oxide, through a screen having 40 wires per inch. These components are dry mixed. Then, anhydrous ethyl alcohol is added to the mixture with stirring to form a uniformly damp mass. The resulting mass is passed through a screen having 20 wires per inch. The resulting granules are air dried overnight at room temperature. The dried granules are then passed through a screen having 20 wires per inch. Finally, 5 grams of magnesium stearate, previously passed through a screen having 60 wires per inch, is tumble mixed into the dried granules. The resulting composition is referred to as the displacement, or push layer granulation.

The two compositions, the drug composition and the displacement composition were manufactured into two batches of tablets fabricated by compressing these granulation composition with $^{11}\!/_{32}$ inch diameter round standard concave tooling on a press. One batch of tablets was made by filling 82.5 mg of push layer granulation into the die cavity and lightly compacting the mass. Then, 165 mg of drug layer granulation was placed over the lightly compacted push layer and laminated to it by compressing both layers with a force of 1 ton. Each of the resulting bilayer tablets of this batch contained 33 mg of nifedipine which comprised a unit dose of 30 mg and an 10 percent overage of 3 mg. Another batch of tablets were made without drug overage. This batch was fabricated using the identical process except that the weight of the drug layer in each tablet was selected to be 150 mg. These tablets without overage contained a unit dose of 30 mg without the 3 mg drug overage. It was observed that the tablets of each batch had the sharp corners which are commonly formed on tablets as a result of the compression step. The sharp corners are commonly referred to in tablet technology as the "land" of the tablet.

Next, both batches were then coated with the rate-controlling membrane of this invention. The membrane formulation consisted of a subcoat and an overcoat. The subcoat formulation was prepared by first dissolving 12 grams of polyethylene glycol having a molecular weight of 400 grams per mole in 1760 grams of water. Then, 14.4 grams of polyoxyethylene (20) sorbitan tristearate was added with stirring while warming the fluid to 40 degrees centigrade. When the 40 degree temperature was reached, 105.6 grams of triacetin was added and the stirring rate was increased. The heat was turned off and the fluid was allowed to cool with stirring for one hour. Stirring was stopped and then the fluid was allowed to cool to room temperature. After standing overnight, the fluid was then stirred for 30 minutes. Then, 108 grams micronized cellulose acetate was slowly added to the vortex of the fluid until fully dispersed in the fluid. The cellulose acetate had a molecular weight of 40,000 grams per mole, an acetyl content 39.8 weight percent, and had been air jet milled to a nominal particle size of 5–10 microns. The resulting dispersion was mixed for one hour. This composition is referred to as the subcoat coating fluid.

Then, in a separate mixing vessel, 1.4 grams of polyethylene glycol in flake form and having a molecular weight of 8,000 grams per mole was dissolved at room temperature with stirring into 186 grams of water. After the dissolution, 12.6 grams of hydroxypropylmethyl cellulose having a hydroxypropoxyl content of 10 weight percent, a methyoxyl content of 29 weight percent, and a molecular weight of 11,900 grams per mole was added with stirring until dissolved. This composition is referred to as the overcoat coating fluid.

Next, the two batches of tablets were simultaneously charged into a fluidized bed coater. The subcoat coating fluid while being continuously stirred was applied by atomizing it through a standard nozzle with air pressure of 0.8 barr at a spray rate of 9 grams per minute. The bed of tablets was fluidized in a current of warm air with an air flow of 140–160 cubic feet per minute, an inlet temperature of 50–51° C., an outlet temperature of 33–34° C. to reach a subcoating thickness of 8 mils. Then, the overcoat coating fluid while being continuously stirred was applied at a spray rate of 3 grams per minutes with an air flow of 130–155 cubic feet per minute, an inlet temperature of 41 degrees centigrade, an outlet temperature of 33 degrees centigrade until an overcoat thickness of 2 mils was accumulated. Each batch was then transferred to a forced air oven thermostated at 50° C. for 4 days. Then, a single, round exit was drilled with a 30 mil diameter drill bit in the center of the drug layer side. This completed fabrication of the dosage form. It was observed that the land of the tablet had formed a template for the membrane coating which coating also retained the shape of the underlying tablet land.

Next, five samples of the dosage forms without drug overage and five samples of the dosage forms with overage were then tested in vitro. Each delivery system was agitated gently in 50 ml of distilled water thermostated at 37° C. for two hours. Then, each system was transferred to a fresh 50 ml receptor and agitated for another 2 hours. This process was repeated until twelve samples of each dosage form had been collected, representing a delivery performance covering a 24-hour period. It was observed that during the initial few hours of the test, the sharp corner of the membrane of each dosage form became rounded as the drug layer was pushed against it internally by the swelling properties of the push layer. rounded corners remained smooth and rounded for the entire duration of the release test.

Upon completion of the release test, each of the above receptor samples were then mixed with 35 ml of polyethylene glycol having a molecular weight of 400 grams per mole. Also, the ten membrane shells of the residuals of the systems were cut open with a razor and the residual tablet material remaining within the membrane shell was quantitatively transferred to a flask containing 50 parts water and 50 parts polyethylene glycol also having a molecular weight of 400 grams per mole. The resulting mixture was stirred until all of the soluble components within the residual shell were flushed from the membrane shells and dissolved. The release receptor solutions and solutions with residuals were then photodegraded by shining a flood light on all the samples for 10 hours to produce a ultraviolet chromophore. The resulting samples were then assayed by ultraviolet spectroscopy at a wavelength 282 nanometers. The release rate data and residual drug data were then plotted and tabulated.

Figure 7:
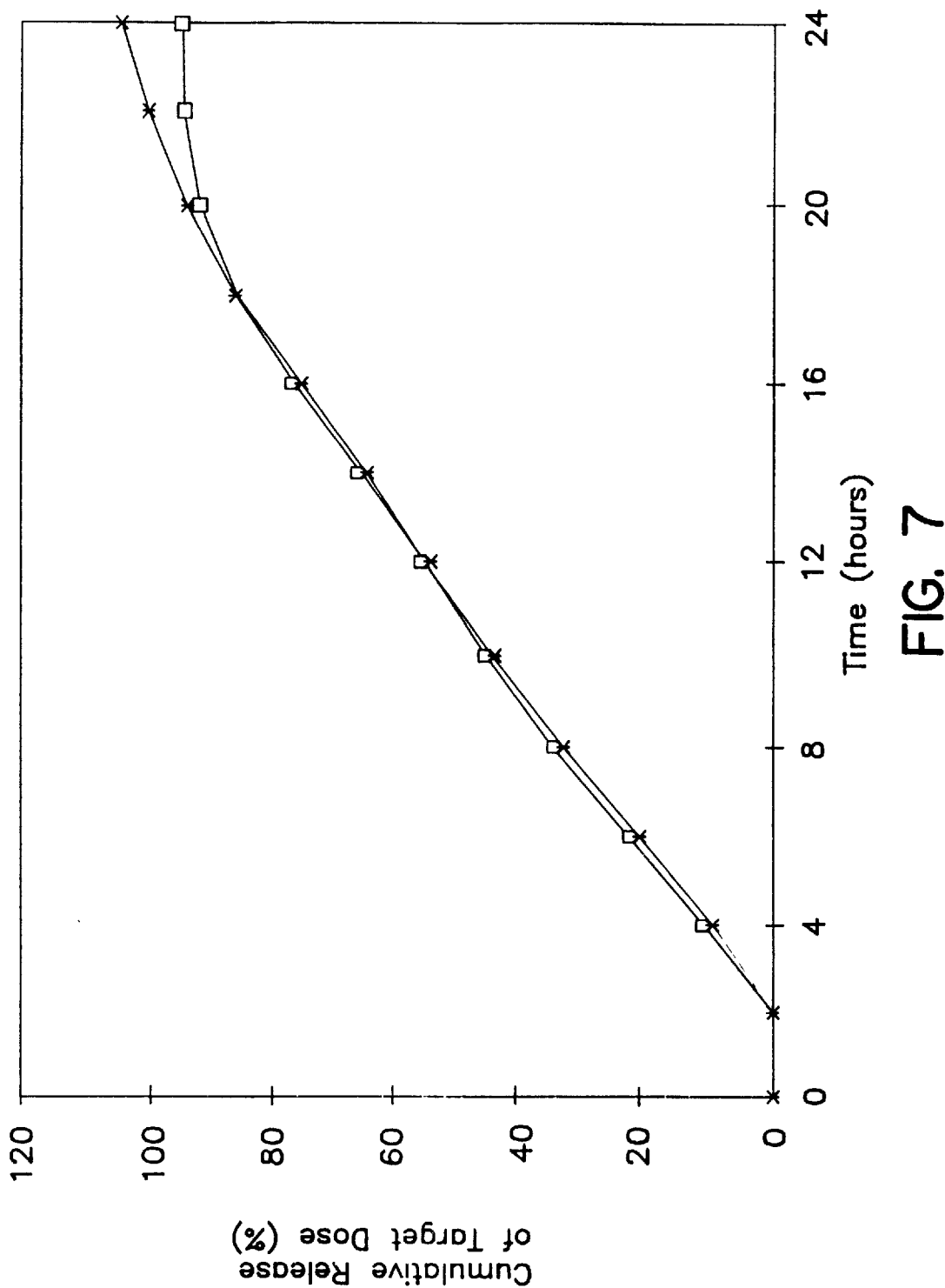
FIG. 7 illustrates the drug release profile from dosage forms over a twenty-four extended drug delivery period.

The in vitro performance results of the release test are plotted in FIG. 7 and tabulated in Tables 1 and 2. In FIG. 7, the cumulative release as a percent of 30 mg target dose is plotted as a function of time where 100% represents 30 mg of drug released over time. The drug of the study was nifedipine. The line with the square symbols represent the average cumulative release of the dosage form manufactured without a drug overage in the dosage form. The line with cross symbols refer to the average cumulative release of the dosage form comprising 10% overage of drug in the dosage form. The release performance is identical through the time course of the test up until the final 4 hours of release. At this point, the performance of the two systems diverge. The system without overage pumps 28.94 mg of the 30 mg target dose, representing more than 96 percent of the target dose. By contrast, the system with overage continues to deliver the drug overage which overage delivery is actually more than it need deliver. The systems with overage formulated in the core delivered 31.64 mg of the target 30 mg dose, representing more than 105 percent of the target dose.

Accompanying Table 1 presents the drug release performance of a dosage form manufactured without overage of drug in the dosage form. The drug in the study was nifedipine. The table plots the cumulative amount in mg released per unit time over time, and the minimum-average-maximum released over time. In the table SD denotes the standard deviation and CV denotes the coefficient of variation. The dosage form exhibited a 0.76 mg average residual and a 29.70 mg average mass balance.

TABLE 1

| | CUMULATIVE AMOUNT RELEASED (MG) | | | | | | | | |
|---|---|---|---|---|---|---|---|---|---|
| TIME | 1 | 2 | 3 | 4 | 5 | MINIMUM | AVERAGE | MAXIMUM | SD | CV |
| 2.00 | .09 | .11 | .11 | .12 | .14 | .09 | .12 | .14 | .018 | .154 |
| 4.00 | 2.28 | 3.15 | 3.11 | 3.54 | 2.87 | 2.28 | 2.99 | 3.54 | .465 | .156 |
| 6.00 | 5.42 | 7.07 | 6.91 | 7.57 | 6.60 | 5.42 | 6.71 | 7.57 | .806 | .120 |
| 8.00 | 8.60 | 10.71 | 10.33 | 11.50 | 10.41 | 8.60 | 10.31 | 11.50 | 1.062 | .103 |
| 10.00 | 11.95 | 13.86 | 13.81 | 14.94 | 13.72 | 11.95 | 13.66 | 14.94 | 1.072 | .079 |
| 12.00 | 14.76 | 16.89 | 17.18 | 18.29 | 16.90 | 14.76 | 16.81 | 18.29 | 1.278 | .076 |
| 14.00 | 17.70 | 19.95 | 20.55 | 21.91 | 20.05 | 17.70 | 20.03 | 21.91 | 1.522 | .076 |
| 16.00 | 20.55 | 23.38 | 24.07 | 25.39 | 23.35 | 20.55 | 23.35 | 25.39 | 1.768 | .076 |
| 18.00 | 23.60 | 26.09 | 26.64 | 27.75 | 26.39 | 23.60 | 26.09 | 27.75 | 1.530 | .059 |
| 20.00 | 26.13 | 27.98 | 28.48 | 28.67 | 28.58 | 26.13 | 27.97 | 28.67 | 1.063 | .038 |
| 22.00 | 27.97 | 29.00 | 28.72 | 28.83 | 28.98 | 27.97 | 28.70 | 29.00 | .424 | .015 |
| 24.00 | 28.70 | 29.15 | 28.83 | 28.92 | 29.11 | 28.70 | 28.94 | 29.15 | .190 | .007 |

In accompanying Table 2, the release-rate performance for a dosage form comprising an overage of drug nifedipine is set forth. The dosage forms exhibited a 1.18 mg average residual and a 32.82 mg average mass balance.

TABLE 2

| | CUMULATIVE AMOUNT RELEASED (MG) | | | | | | | | |
|---|---|---|---|---|---|---|---|---|---|
| TIME | 1 | 2 | 3 | 4 | 5 | MINIMUM | AVERAGE | MAXIMUM | SD | CV |
| 2.00 | .11 | .14 | .12 | .12 | .14 | .11 | .13 | .14 | .013 | .102 |
| 4.00 | 1.98 | 3.00 | 2.92 | 2.33 | 2.28 | 1.98 | 2.50 | 3.00 | .439 | .175 |
| 6.00 | 5.71 | 7.12 | 6.52 | 5.91 | 5.84 | 5.71 | 6.22 | 7.12 | .590 | .095 |
| 8.00 | 9.25 | 11.27 | 10.28 | 9.43 | 9.36 | 9.25 | 9.92 | 11.27 | .858 | .087 |
| 10.00 | 12.72 | 15.11 | 13.37 | 12.73 | 12.72 | 12.72 | 13.33 | 15.11 | 1.032 | .077 |
| 12.00 | 16.00 | 18.63 | 16.39 | 16.23 | 15.93 | 15.93 | 16.64 | 18.63 | 1.131 | .068 |
| 14.00 | 19.18 | 22.21 | 19.16 | 19.49 | 18.93 | 18.93 | 19.80 | 22.21 | 1.364 | .069 |
| 16.00 | 22.32 | 25.77 | 22.52 | 22.86 | 21.94 | 21.94 | 23.08 | 25.77 | 1.537 | .067 |
| 18.00 | 25.50 | 28.56 | 25.72 | 26.05 | 25.05 | 25.05 | 26.18 | 28.56 | 1.382 | .053 |
| 20.00 | 27.94 | 30.71 | 28.12 | 28.56 | 27.73 | 27.73 | 28.61 | 30.71 | 1.213 | .042 |
| 22.00 | 29.92 | 31.70 | 29.98 | 30.59 | 29.75 | 29.75 | 30.39 | 31.70 | .799 | .026 |
| 24.00 | 31.62 | 31.87 | 31.35 | 32.04 | 31.31 | 31.31 | 31.64 | 32.04 | .318 | .010 |

The performance of the dosage form can also be expressed in terms of the amount of drug initially formulated within the dosage form rather than based on the target 30 mg dose. The dosage form without overage delivered 28.94 mg of the 29.7 mg of the assayed quantity (the sum total of the cumulative drug release and the residual drug not released) or more than 97 percent of the loading. Similarly, the dosage form with overage delivered 31.64 of the 32.32 assayed quantity or more than 97 percent of the loading. Thus, it is clear that dosage forms delivered more than 97 percent of the loading whether an overage was initially present or not. These data demonstrate that by using this specialized membrane, it is not necessary to formulate a 10% overage initially in the dosage form to achieve the target delivery dose.

EXAMPLE 4

Figure 8:
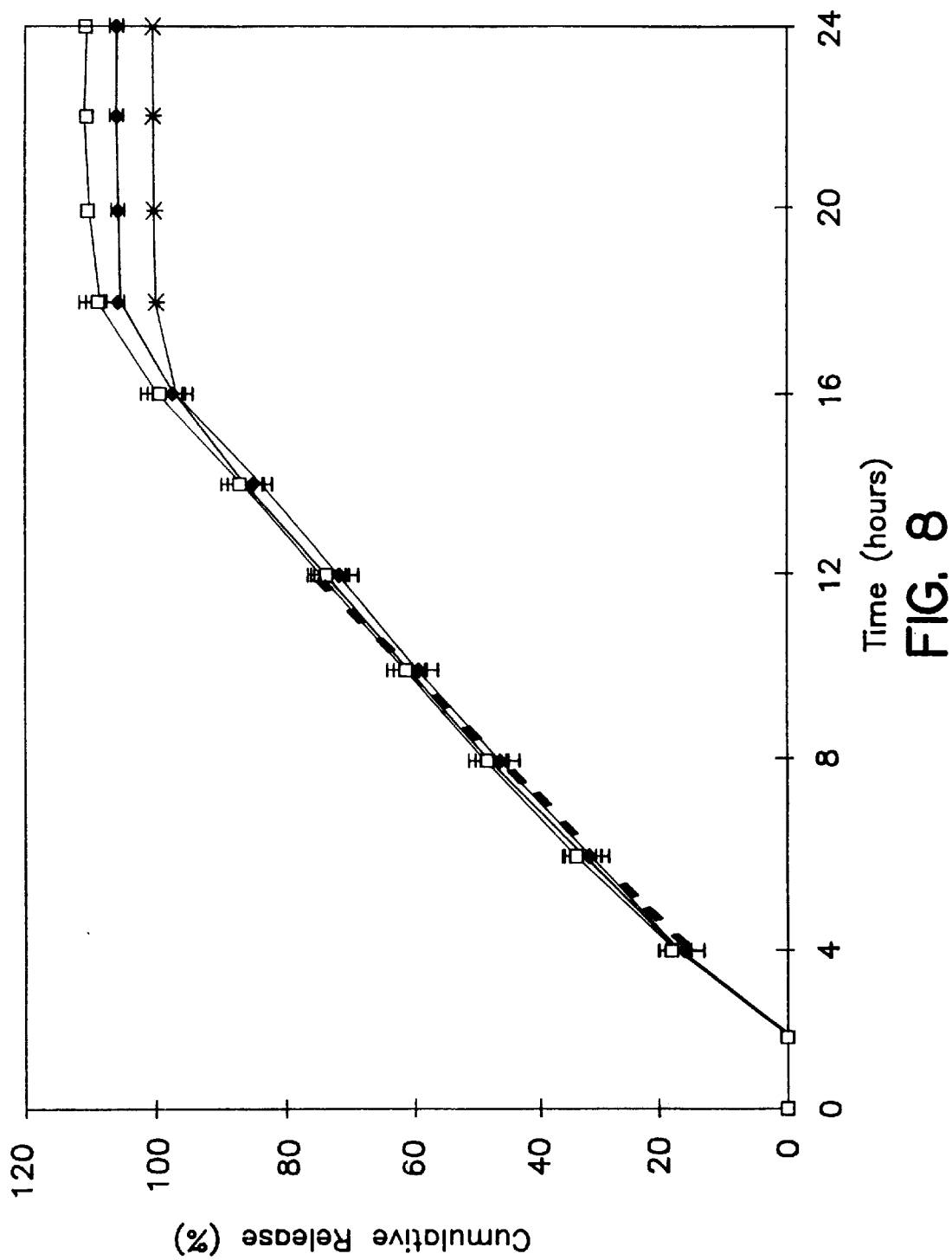
FIG. 8 illustrates the drug release profiles for three different dosage forms manufactured by the invention.

The procedure of Example 2 was followed in this example to provide a dosage form comprising (1) a 300 mg drug composition comprising 20.15 wt % nifedipine, 74.55 wt % polyethylene of 200,000 molecular weight, 5.04 wt % hydroxypropylmethylcellulose of 11,200 molecular weight, and 0.26 wt % magnesium stearate; (2) a 165 mg displacement composition comprising 64.50 wt % polyethylene oxide of 7,500,000 molecular weight, 29.00 wt % sodium chloride, 5.00 wt % hydroxypropylmethylcellulose of 11,200 molecular weight, 1.00 wt % ferric oxide, and 0.50 wt % magnesium stearate; (3) a 109.6 mg inner membrane comprising 45.0 wt % cellulose acetate consisting, 39.8% acetyl content, 41.0 wt % triacetin, 6.0 wt % polyoxyethylene sorbitan monostearate, and 8.0 wt % polyethylene glycol of 400 molecular weight; (4) a 9.3 mg outer membrane comprising 90.0 wt % hydroxypropyl-methylcellulose 606 of 11,900 molecular weight and 10.0 wt % polyethylene glycol possessing an 8,000 molecular weight; (5) a 30 mil (0.762 mm) exit; and, (6) a 13.6 hr release rate of 4.181 mg/hr. The dosage form comprised zero percent drug overage. The procedure was followed to provide a dosage form comprising a five percent drug overage and a ten percent drug overage. Accompanying FIG. 8 plots the release profile for a dosage form comprising 60 mg of nifidipine, wherein the line with crosses denotes zero drug overage, the line with diamonds denotes five percent drug overage, and the line with squares denotes ten percent drug overage.

EXAMPLE 5

The manufacturing procedures described herein are followed to provide a dosage form according to the invention to comprise a drug selected from the group consisting of tetrazosin hydrochloride, felodipine, omeprazole, pergolide, clonidine hydrochloride, pravastatin sodium, sumatriptan succinate, acyclovir, diltiazem, oxybutynin, verapamil, lisinopril, finasteride, simvastatin, doxazosin mesylate, and seleziline hydrochloride.

METHOD OF PRACTICING THE INVENTION

The invention pertains additionally to the use of the therapeutic dosage form by providing a method for delivering a drug orally to a warm-blooded animal, including a human patient in need of therapy. The method comprises admitting orally into a patient a dosage form comprising a semipermeable membrane that surrounds a therapeutic composition comprising a dose of drug that is administered totally to a patient. The dosage form imbibes fluid through the semipermeable membrane into the dosage form in response to the concentration gradient across the semipermeable membrane. The therapeutic composition in the dosage form generates osmotic energy that causes the therapeutic composition to be administered through an exit in the membrane over a prolonged period of time up to 30 hours to provide controlled and sustained release therapy.

In summary, it will be appreciated that the present invention contributed to the art an unobvious dosage form that possesses practical utility, can administer a drug at a dose-metered release rate per unit time. While the invention has been described and pointed out in detail with reference to operative embodiments thereof, it will be understood by those skilled in the art that various changes, modifications, substitution and omissions can be made without departing from the spirit of the invention. It is intended, therefore, that the invention embrace those equivalents within the scope of the claims which follow.

We claim:

1. A dosage form for delivering a dose of 0.5 mg to 650 mg of a drug comprising a particle size of up to 5 microns, wherein the dosage form comprises a membrane that defines the shape of the dosage form, said membrane comprising a means for changing the shape of the dosage form from a non-rounded dosage form to a rounded dosage form that enhances the delivery of the drug at a controlled and sustained rate over an extended time.

2. A dosage form for delivering a maximum dose of 0.5 mg to 650 mg of a drug in vivo, wherein the dosage form comprises means for changing the shape of the dosage form as shown in FIG. 6 from shape 12a to shape 12b, whereby less drug is maintained in the dosage form for delivering the maximum dose of 0.5 mg to 650 mg of the drug over an extended time.

3. A process for increasing the dose of drug delivered from a dosage form possessing controlled-sustained release delivery, wherein the dosage form comprises: a membrane and a dose of drug, and wherein the process comprises: blending means with the membrane for making the membrane flexible and distensible; shaping the membrane to provide a shaped membrane; and changing the dosage form from a non-rounded dosage form to a rounded dosage form thereby increasing the dose of drug delivered at a controlled-release rate from the dosage form.

4. A method for administering the maximum dose of a drug to a patient, wherein the method comprises administering orally to the patient a controlled-sustained release dosage form comprising: a dose of 0.5 mg to 650 mg of a drug, and a membrane comprising a means for changing the dosage form from a non-rounded dosage form to a rounded dosage form for delivering the maximum dose of 0.5 mg to 650 mg of the drug at a controlled-sustained release rate over an extended time.

5. The method according to claim 4, wherein the means comprises a plasticizer.

6. The method according to claim 4, wherein the means comprises a plasticizer selected from the group consisting of adipic acid, azelaic acid, benzoic acid, citric acid, epoxy, glycol, glycerol, phosphoric acid, phthalic acid, ricinoleic acid, sebacic acid, and trimellitic acid plasticizers.

* * * * *